United States Patent
Glauser et al.

(10) Patent No.: US 9,468,706 B2
(45) Date of Patent: Oct. 18, 2016

(54) PHOSPHORYL CHOLINE COATING COMPOSITIONS

(71) Applicant: Abbott Cardiovascular Systems Inc., Santa Clara, CA (US)

(72) Inventors: Thierry Glauser, Redwood City, CA (US); Stephen Dirk Pacetti, San Jose, CA (US); Syed Faiyaz Ahmed Hossainy, Hayward, CA (US); Ni Ding, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/664,554

(22) Filed: Mar. 20, 2015

(65) Prior Publication Data

US 2015/0328375 A1 Nov. 19, 2015

Related U.S. Application Data

(63) Continuation of application No. 10/807,362, filed on Mar. 22, 2004, now abandoned.

(51) Int. Cl.
*A61L 31/10* (2006.01)
*A61L 31/14* (2006.01)
*A61L 33/08* (2006.01)
*A61L 33/00* (2006.01)
*A61L 31/16* (2006.01)
*A61L 27/34* (2006.01)

(52) U.S. Cl.
CPC .............. *A61L 31/10* (2013.01); *A61L 27/34* (2013.01); *A61L 31/148* (2013.01); *A61L 31/16* (2013.01); *A61L 33/0011* (2013.01); *A61L 33/08* (2013.01); *A61L 2300/40* (2013.01); *A61L 2300/42* (2013.01); *A61L 2300/604* (2013.01); *A61L 2300/606* (2013.01); *A61L 2400/18* (2013.01)

(58) Field of Classification Search
None
See application file for complete search history.

(56) References Cited

U.S. PATENT DOCUMENTS

| | | | |
|---|---|---|---|
| 4,499,251 A * | 2/1985 | Omura | A61L 24/06 106/35 |
| 4,613,665 A | 9/1986 | Larm | |
| 4,664,630 A * | 5/1987 | Lokken | A61K 6/0026 106/35 |
| 4,765,983 A * | 8/1988 | Takayanagi | A61K 31/57 424/434 |
| 4,916,193 A | 4/1990 | Tang et al. | |
| 4,994,071 A | 2/1991 | MacGregor et al. | |
| 5,092,877 A | 3/1992 | Pinchuk et al. | |
| 5,163,952 A | 11/1992 | Froix et al. | |
| 5,182,317 A | 1/1993 | Winters et al. | |
| 5,262,451 A | 11/1993 | Winters et al. | |
| 5,272,012 A | 12/1993 | Opolski | |
| 5,302,385 A | 4/1994 | Khon et al. | |
| 5,304,121 A | 4/1994 | Sahatjian et al. | |
| 5,338,770 A | 8/1994 | Winters et al. | |
| 5,455,040 A | 10/1995 | Marchant et al. | |
| 5,464,650 A | 11/1995 | Berg et al. | |
| 5,562,922 A | 10/1996 | Lambert | |
| 5,575,818 A | 11/1996 | Pinchuk | |
| 5,702,754 A | 12/1997 | Zhong | |
| 5,741,881 A * | 4/1998 | Patnaik | A61L 27/34 128/DIG. 22 |
| 5,812,317 A | 9/1998 | Billingsley et al. | |
| 5,869,132 A | 2/1999 | Watanabe et al. | |
| 5,980,972 A | 11/1999 | Ding | |
| 5,997,517 A | 12/1999 | Whitbourne | |
| 6,001,117 A | 12/1999 | Huxel et al. | |
| 6,099,562 A | 8/2000 | Ding et al. | |
| 6,110,483 A | 8/2000 | Whitbourne et al. | |
| 6,197,332 B1 * | 3/2001 | Zuckermann | C12N 15/87 424/450 |
| 6,270,788 B1 | 8/2001 | Koulik et al. | |
| 6,273,913 B1 | 8/2001 | Wright et al. | |
| 6,274,164 B1 | 8/2001 | Novich | |
| 6,306,176 B1 | 10/2001 | Whitbourne | |
| 6,383,215 B1 | 5/2002 | Sass et al. | |
| 6,494,862 B1 | 12/2002 | Ray et al. | |
| 6,497,729 B1 | 12/2002 | Moussy et al. | |
| 6,503,538 B1 | 1/2003 | Chu et al. | |
| 6,544,223 B1 | 4/2003 | Kokish | |
| 6,544,543 B1 | 4/2003 | Mandrusov et al. | |
| 6,544,862 B1 | 4/2003 | Bryan | |
| 6,656,216 B1 | 12/2003 | Hossainy | |
| 6,656,506 B1 | 12/2003 | Wu et al. | |
| 6,663,662 B2 | 12/2003 | Pacetti et al. | |
| 6,663,880 B1 | 12/2003 | Roorda et al. | |
| 6,673,154 B1 | 1/2004 | Pacetti et al. | |

(Continued)

FOREIGN PATENT DOCUMENTS

| | | |
|---|---|---|
| EP | 0 623 354 | 11/1994 |
| EP | 0 947 205 | 10/1999 |

(Continued)

OTHER PUBLICATIONS

Spiegel et al. Journal of Biological Chemistry 2002 277(29):25851-25854.*
U.S. Appl. No. 09/894,293, filed Jun. 27, 2001, Hossainy.
U.S. Appl. No. 09/966,786, filed Sep. 27, 2001, Hossainy.
U.S. Appl. No. 09/967,632, filed Sep. 28, 2001, Pacetti.
U.S. Appl. No. 10/104,772, filed Mar. 20, 2002, Dutta.
U.S. Appl. No. 10/246,883, filed Sep. 18, 2002, Taylor.
U.S. Appl. No. 10/260,182, filed Sep. 27, 2002, Hossainy.
U.S. Appl. No. 10/271,851, filed Oct. 15, 2002, Roorda.
U.S. Appl. No. 10/286,058, filed Oct. 31, 2002, Pacetti et al.
U.S. Appl. No. 10/316,739, filed Dec. 10, 2002, Zhang et al.

(Continued)

*Primary Examiner* — Robert A Wax
*Assistant Examiner* — Caralynne Helm
(74) *Attorney, Agent, or Firm* — Squire Patton Boggs (US) LLP

(57) ABSTRACT

A polymer comprising phospholipid moieties and a biocompatible polymer backbone, a composition comprising the polymer and optionally a bioactive agent, an implantable devices such as a drug eluting stent comprising thereon a coating comprising the polymer and optionally a bioactive agent, and a method of using the device for the treatment of a disorder in a human being are provided.

18 Claims, No Drawings

(56) References Cited

U.S. PATENT DOCUMENTS

| | | |
|---|---|---|
| 6,703,040 B2 | 3/2004 | Katsarava |
| 6,712,845 B2 | 3/2004 | Hossainy |
| 6,743,462 B1 | 6/2004 | Pacetti |
| 6,753,071 B1 | 6/2004 | Pacetti |
| 6,758,859 B1 | 7/2004 | Dang et al. |
| 6,790,228 B2 | 9/2004 | Hossainy |
| 6,818,063 B1 | 11/2004 | Kerrigan |
| 6,824,559 B2 | 11/2004 | Michal |
| 6,926,919 B1 | 8/2005 | Hossainy et al. |
| 6,972,054 B2 | 12/2005 | Kerrigan |
| 7,005,137 B1 | 2/2006 | Hossainy et al. |
| 7,022,334 B1 | 4/2006 | Ding |
| 7,056,591 B1 | 6/2006 | Pacetti et al. |
| 7,060,093 B2 | 6/2006 | Dang |
| 7,074,276 B1 | 7/2006 | Van Sciver et al. |
| 7,115,300 B1 | 10/2006 | Hossainy et al. |
| 7,135,038 B1 | 11/2006 | Limon |
| 7,166,680 B2 | 1/2007 | Desnoyer |
| 7,169,178 B1 | 1/2007 | Santos et al. |
| 7,175,874 B1 | 2/2007 | Pacetti |
| 7,201,935 B1 | 4/2007 | Claude et al. |
| 7,202,325 B2 | 4/2007 | Hossainy |
| 7,217,426 B1 | 5/2007 | Hossainy |
| 7,232,490 B1 | 6/2007 | Hossainy |
| 7,232,573 B1 | 6/2007 | Ding |
| 7,244,443 B2 | 7/2007 | Pacetti |
| 7,247,313 B2 | 7/2007 | Roorda et al. |
| 7,255,891 B1 | 8/2007 | Pacetti |
| 7,261,946 B2 | 8/2007 | Claude |
| 7,288,609 B1 | 10/2007 | Pacetti |
| 7,294,329 B1 | 11/2007 | Ding |
| 7,311,980 B1 | 12/2007 | Hossainy et al. |
| 7,323,209 B1 | 1/2008 | Esbeck et al. |
| 7,329,413 B1 | 2/2008 | Pacetti |
| 7,335,265 B1 | 2/2008 | Hossainy |
| 7,335,391 B1 | 2/2008 | Pacetti |
| 7,341,630 B1 | 3/2008 | Pacetti |
| 7,354,480 B1 | 4/2008 | Kokish et al. |
| 7,390,524 B1 | 6/2008 | Chen |
| 7,396,539 B1 | 7/2008 | Hossainy et al. |
| 7,396,541 B2 | 7/2008 | Hossainy et al. |
| 7,431,959 B1 | 10/2008 | Dehnad |
| 7,481,835 B1 | 1/2009 | Pacetti et al. |
| 7,494,665 B1 | 2/2009 | Ding et al. |
| 7,504,125 B1 | 3/2009 | Pacetti et al. |
| 7,563,454 B1 | 7/2009 | Pacetti |
| 7,628,859 B1 | 12/2009 | Hossainy et al. |
| 7,645,504 B1 | 1/2010 | Pacetti |
| 7,713,541 B1 | 5/2010 | Pacetti et al. |
| 7,722,894 B2 | 5/2010 | Wang et al. |
| 7,781,551 B2 | 8/2010 | Pacetti et al. |
| 7,785,512 B1 | 8/2010 | Pathak et al. |
| 7,850,643 B1 | 12/2010 | Pacetti et al. |
| 7,910,678 B2 | 3/2011 | Pacetti |
| 7,928,176 B2 | 4/2011 | Pacetti |
| 8,048,975 B2 | 11/2011 | Pacetti |
| 8,063,151 B2 | 11/2011 | Pacetti |
| 8,071,705 B2 | 12/2011 | Pacetti |
| 8,101,156 B2 | 1/2012 | Pacetti |
| 8,197,880 B2 | 6/2012 | Pacetti et al. |
| 8,202,956 B2 | 6/2012 | Pacetti |
| 8,339,584 B2 | 12/2012 | Christian et al. |
| 8,431,665 B2 | 4/2013 | Pacetti et al. |
| 8,464,839 B2 | 6/2013 | Ueno |
| 8,506,617 B1 | 8/2013 | Michal et al. |
| 8,569,435 B2 | 10/2013 | Pacetti |
| 8,658,749 B2 | 2/2014 | Pacetti |
| 8,685,428 B2 | 4/2014 | Zhang et al. |
| 9,180,225 B2 | 11/2015 | Pacetti |
| 2001/0007083 A1 | 7/2001 | Roorda |
| 2001/0029351 A1 | 10/2001 | Falotico et al. |
| 2001/0044651 A1 | 11/2001 | Steinke |
| 2002/0193336 A1* | 12/2002 | Elkins .............. A61F 2/91 514/44 R |
| 2003/0021762 A1 | 1/2003 | Luthra |
| 2003/0073961 A1 | 4/2003 | Happ |
| 2003/0088307 A1* | 5/2003 | Shulze .............. A61F 2/91 623/1.15 |
| 2003/0104028 A1 | 6/2003 | Hossainy et al. |
| 2003/0105518 A1 | 6/2003 | Dutta |
| 2003/0158517 A1 | 8/2003 | Kokish |
| 2004/0024450 A1* | 2/2004 | Shulze .............. A61F 2/90 623/1.42 |
| 2004/0047980 A1 | 3/2004 | Pacetti |
| 2004/0052858 A1 | 3/2004 | Wu et al. |
| 2004/0054104 A1 | 3/2004 | Pacetti |
| 2004/0060508 A1 | 4/2004 | Pacetti |
| 2004/0062853 A1 | 4/2004 | Pacetti et al. |
| 2004/0063805 A1 | 4/2004 | Hossainy |
| 2004/0071861 A1 | 4/2004 | Mandrusov |
| 2004/0072922 A1 | 4/2004 | Hossainy |
| 2004/0073298 A1 | 4/2004 | Hossainy |
| 2004/0086542 A1 | 5/2004 | Hossainy |
| 2004/0096476 A1 | 5/2004 | Uhrich |
| 2004/0142015 A1 | 7/2004 | Hossainy et al. |
| 2004/0162609 A1 | 8/2004 | Hossainy et al. |
| 2004/0180039 A1 | 9/2004 | Toner et al. |
| 2004/0182312 A1 | 9/2004 | Pacetti et al. |
| 2004/0191405 A1 | 9/2004 | Kerrigan |
| 2004/0253203 A1 | 12/2004 | Hossainy |
| 2005/0021127 A1 | 1/2005 | Kawula |
| 2005/0025799 A1 | 2/2005 | Hossainy |
| 2005/0032826 A1 | 2/2005 | Mollison et al. |
| 2005/0074544 A1 | 4/2005 | Pacetti et al. |
| 2005/0092406 A1 | 5/2005 | Fleming et al. |
| 2005/0112170 A1 | 5/2005 | Hossainy et al. |
| 2005/0112171 A1 | 5/2005 | Tang et al. |
| 2005/0118344 A1 | 6/2005 | Pacetti |
| 2005/0137381 A1 | 6/2005 | Pacetti |
| 2005/0147647 A1 | 7/2005 | Glauser et al. |
| 2005/0169957 A1 | 8/2005 | Hossainy |
| 2005/0175666 A1 | 8/2005 | Ding |
| 2005/0208091 A1 | 9/2005 | Pacetti |
| 2005/0208093 A1 | 9/2005 | Glauser |
| 2005/0208095 A1 | 9/2005 | Hunter et al. |
| 2005/0214339 A1 | 9/2005 | Tang et al. |
| 2005/0226991 A1 | 10/2005 | Hossainy et al. |
| 2005/0244363 A1 | 11/2005 | Hossainy et al. |
| 2005/0265960 A1 | 12/2005 | Pacetti et al. |
| 2005/0271700 A1 | 12/2005 | Desnoyer et al. |
| 2005/0287184 A1 | 12/2005 | Hossainy et al. |
| 2006/0002968 A1 | 1/2006 | Stewart et al. |
| 2006/0034888 A1 | 2/2006 | Pacetti et al. |
| 2006/0043650 A1 | 3/2006 | Hossainy et al. |
| 2006/0062824 A1 | 3/2006 | Pacetti et al. |
| 2006/0089485 A1 | 4/2006 | Desnoyer et al. |
| 2006/0095122 A1 | 5/2006 | Pacetti |
| 2006/0115449 A1 | 6/2006 | Pacetti |
| 2006/0134165 A1 | 6/2006 | Pacetti |
| 2006/0136048 A1 | 6/2006 | Pacetti et al. |
| 2007/0005130 A1 | 1/2007 | Glauser et al. |
| 2007/0032853 A1 | 2/2007 | Hossainy et al. |
| 2008/0286332 A1 | 11/2008 | Pacetti |
| 2010/0125329 A1 | 5/2010 | Lin et al. |

FOREIGN PATENT DOCUMENTS

| | | |
|---|---|---|
| JP | 09-003132 | 7/1997 |
| JP | 09-183819 | 7/1997 |
| JP | 2001-200480 | 7/2001 |
| JP | 2002-080402 | 3/2002 |
| WO | WO 98-22516 | 5/1998 |
| WO | WO 99-26637 | 6/1999 |
| WO | WO 00-56283 | 9/2000 |
| WO | WO 01-52915 | 7/2001 |
| WO | WO 01-78800 | 10/2001 |
| WO | WO 01-85218 | 11/2001 |
| WO | WO 02-40558 | 5/2002 |
| WO | WO 02-067908 | 9/2002 |
| WO | WO 02-071944 | 9/2002 |
| WO | WO 02-087586 | 11/2002 |
| WO | WO 03-022324 | 3/2003 |
| WO | WO03082368 | 10/2003 |
| WO | WO 2004-009664 | 1/2004 |

(56) References Cited

FOREIGN PATENT DOCUMENTS

| WO | WO 2004-021976 | 3/2004 |
|---|---|---|
| WO | WO 2005-000939 | 1/2005 |
| WO | WO 2008-144130 | 11/2008 |

OTHER PUBLICATIONS

U.S. Appl. No. 10/375,496, filed Feb. 26, 2003, Esbeck.
U.S. Appl. No. 10/376,348, filed Feb. 26, 2003, Ding et al.
U.S. Appl. No. 10/705,546, filed Nov. 10, 2003, Kwok et al.
U.S. Appl. No. 10/729,728, filed Dec. 5, 2003, Pacetti.
U.S. Appl. No. 10/835,229, filed Apr. 28, 2004, Prabhu et al.
U.S. Appl. No. 10/877,419, filed Jun. 25, 2004, Pacetti.
U.S. Appl. No. 10/883,242, filed Jun. 30, 2004, Roorda et al.
U.S. Appl. No. 10/913,607, filed Aug. 5, 2004, Pacetti et al.
U.S. Appl. No. 10/932,364, filed Aug. 31, 2004, Foreman et al.
"Cardiologist draw-up the dream stent," Dialog Web, Aug. 25, 2003, URL: www.dialogweb.com/cgi/document?req=1061848202959, 1 pp.
"Heparin—coated stents cut complications by 30%," DialogWeb, Clinica 732, p. 17, 1996 Abstract, URL: http://www.dialogweb.com/cgi/document?req=1061847871753, Aug. 25, 2003, 1 pp.
"Rolling therapeutic agent loading device for therapeutic agent delivery or coated stent," Research Disclosure, Jun. 2000, pp. 1-2.
"Stenting continues to dominate cariology," Clinica 720, p. 22, Sep. 2, 1996, abstract, URL:http://www.dialogweb.com/cgi/document?req=1061848017752, Aug. 25, 2003, 2 pp.
Aoyagi, Takao et al. "Preparation of cross-linked aliphatic polyester and application to thermos-responsive material," Journal of Controlled Release, 1994, vol. 32, pp. 87-96.
Barath, M.D., Peter et al. "Low Dose of Antitumor Agents Prevents Smooth Muscle Cell Proliferation After Endothelial Injury," JACC, vol. 13, No. 2, 1 pp.
Barbucci et al."Coating of commercially available materials with a new heparinizable material," Journal of Biomedical Materials Research, vol. 25, pp. 1259-1274.
Berrocal et al., "Improving the Blood Compatibility of Ion-Selective Electrodes by Employing Poly(MPC-co-BMA), a Copolymer Containing Phosphorylcholine, as a Membrane Coating," Anal. Chem., 2002, vol. 74, No. 15, pp. 3644-3648.
Chung, Joo et al. "Inner core segment design for drug delivery control of thermos-responsive polymeric micelles," Journal of Controlled Release, 2000, vol. 65, 93-103.
Dev, M.D., Vishva et al. "Kinetics of Drug Delivery to the Arterial Wall Via Polyurethane-Coated Removable Nitinol Stent: Comparative Study of Two Drugs," Catheterization and Cardiovascular Diagnosis, 1995, vol. 34, pp. 272-278.
Dichek, David et al. "Seeding of Intravascular Stents with Genetically Engineered Endothelial Cells," Circulation, 1989, vol. 80, No. 5, pp. 1347-1353.
Durrani, Aziz et al. "Biomembranes as models for polymer surfaces," Biomaterials, 1966, vol. 7, pp. 121-126.
European Search Report for appl. 05 728 269.1, mailed Jan. 19, 2009, 5 pages.
Francois, P., et al. *Biomaterials*, 1996, vol. 17, pp. 67-678.
Freemantle, M., "Polymers Exploited for Drug Delivery: Biocompatibility and Biodegradability are Key Elements in Design of Polymers for Therapeutics," Chemical and Engineering News: 83(16): 45-47 (Apr. 18, 2005).
Gautier et al. Journal of Biomaterial Science Polymer Edition 2003, 14:63-83.
Gisselfalt et al."Effect of Soft Segment Length and Chain Extender Structure on Phase Separation and Morphology in Poly(urethane urea)s" Macromolecular Materials Engineering, 2003, vol. 288, pp. 265-271.
Gravlee, G.P. "Heparin-Coated Cardiopulmonary Bypass Circuits," Journal of Cardiothoracic and Vascular Anesthesia, vol. 8, No. 2, pp. 213-222.

Helmus, Overview of Biomedical Materials, "Medical Device Design—A system Approach: Central Venous Catheters," 22$^{nd}$ International Societyfor the Advancement of Material and Process Engineering Technical Conference, mrs. Bulletin-Sep. 1991, pp. 33-38.
Herdeg, C. et al. "Antiproliferative stent coatings: Taxol and related comounds," Semin Intervent Cardiol, 1998, vol. 3, pp. 197-199.
Hilborn et al., "Biodegradable Phosphatidylcholine Functional Poly (ε-Caprolactone)", Pol. Mat. Science and Eng. vol. 88, 2003, pp. 109-110.
Hubbel, J.A., "Pharmacologic Modification of Materials," Cardiovascular Pathology; Chapter 11, vol. 2, No. 3 (Suppl.), 1993, pp. 121S-127S.
Inoue, Tadaaki et al. "An AB block copolymer of oligo(methyl methacrylate) and poly(acrylic acid) for micellar deliver of hydrophobic drugs," Journal of Controlled Release, 1998, vol. 51, pp. 221-229.
International Search Report and Written Opinion of a PCT/US2005/008844, filed Mar. 17, 2005, mailed Sep. 13, 2005.
Iwasaki, et al, "Molecular Design and Preparation of Bioinspired Phospholipid Polymer as Novel Biomaterials", *Polymer Preprints, Soc. of Polymer Science*, 2001, vol. 42, No. 2, pp. 117-118.
Kataoka, Kazunori et al. "Block copolymer micelles as vehicles for drug deliver," Journal of Controlled Release, 1993, vol. 24, pp. 119-132.
Lamberg et al. Glycosaminoglycans. A Biochemical and Clinical Review, *Journal of Investigative Dermatology*, 1974, vol. 63, No. 6, pp. 433-449.
Lee et al. "Synthesis and Degradation of End-Group-Functionalized Polyactide," *Journal of Polymer Science*, 2001, vol. 39, pp. 973-985.
Levy, Robert, et al. "Strategies for Treating Arterial Restenosis Using Polymeric Controlled Release Implants," Biotechnology and Bioactive Polymers, 1994, pp. 259-267.
Li et al., "Synthesis and Hemocompatibility Evaluation of Novel Segmented Polyurethanes with Phosphatidylcholine Polar Headgroups", Chemistry of Materials, 1998, vol. 10, pp. 1596-1603.
Liu, Hongbo et al. "Drug releae characteristics of unimolecular polymeric micelles," Journal of Controlled Release, 2000, vol. 68, pp. 167-174.
Macrconi, W. et al. "Covalent bonding of heparin to a vinyl copolymer for biomedical applications," Biomaterials, 1997, vol. 18, pp. 885-890.
Matsumaru, Yuji et al. "Embolic materials for endovascular treatment of cerebral lesions," J. Biomater. Sci. Polymer Edu., 1997, vol. 8, No. 7, pp. 555-569.
Miyazaki, Shozo et al. "Antitumor Effect of Implanted Ethylene—Vinyl Alcohol Copolymer Matrices Containing Anticancer Agents on Ehrlich Ascites Carcinoma and P388 Leukemia in Mice," Chem. Pharm Bull., 1985, vol. 33, No. 6, pp. 2491-2499.
Miyazawa, Norio et al. "Effects of Pemirolast and Tranilast on Intimal Thickening After Arterial Injury in the Rat," Journal of Cardiovascular Pharmacology, 1997, pp. 57-162.
Nordrehaug, J.E. et al. "A novel biocompatible coating applied to coronary stents," Coronary Stents, pp. 321.
Ohsawa, et al. "Interventional Cariology—Preventive effects of antiallergic drug, pemirolast potassium, on restenosis after percutaneous transluminal coronary angioplasty," American Heart Journal, vol. 136, No. 6, pp. 1082-1087.
Ozaki, Yukio et al. "New Stent Technologies," Progress in Cardiovascular Diseases, 1996, vol. XXXIX, No. 2, pp. 129-140.
Park et al. "Blood compatibility of SPUU-PEO-heparin graft copolymers," *Journal of Biomedical Materials Research*, 1992, vol. 26, pp. 739-756.
Pechar, Michal et al. "Poly(ethylene glycol) Multiblock Copolymer as a Carrier of Anti-Cancner Drug Doxorubicin," Bioconjugate Chemistry, 2000, vol. 11, No. 2, pp. 132-139.
Peng, et al. "Role of polymers in improving the results of stenting in coronary arteries," Biomaterials, 1996, vol. 17, pp. 685-694.

(56) References Cited

OTHER PUBLICATIONS

Ruiz et al., "Phosphorylcholine-containing polyurethanes for the control of protein adsorption and cell attachment via photoimmobilized laminin oligopeptides," J. Biomater. Sci. Polym. Edn., 1999, vol. 10, No. 9, pp. 931-955.

Shigeno, Taku "Prevention of Cetebrovascular Spasm by Bosentan, Novel Endothelin Recptor," CA 125:212307.

Thomas, Clifford N., "Local Delivery of Heparin with a PTCA Infusion Balloon Inhibits Platelet-dependent Thrombosis," JACC, 1994, Abstract, 2 pp.

Van Beusekom et al. "Coronary stent coatings," Coronary Artery Disease, 1994, vol. 5, No. 7, pp. 590-596.

Wilensky, Robert et al. "Methods and Devices for Local Drug Delivery in Coronary and Peripheral Arteries," TCM, 1993, vol. 3, No. 5, pp. 163-170.

Yokoyama, et al. "Characterization of physical entrapment and chemical conjugation of Adriamycin in polymeric micelles and their design for in vivo delivery to a solid tumor," Journal of Controlled Release, 1998, vol. 50, pp. 79-92.

* cited by examiner

PHOSPHORYL CHOLINE COATING COMPOSITIONS

CROSS-REFERENCE TO RELATED APPLICATION

This application is a continuation of U.S. patent application Ser. No. 10/807,362, filed on Mar. 22, 2004, published as U.S. patent application publication no. US 2005-0208093 A1 on Sep. 22, 2005, and which is incorporated by reference herein in its entirety, expressly including drawings, and is incorporated by reference herein for all purposes.

BACKGROUND OF THE INVENTION

1. Field of the Invention

This invention generally relates to a composition comprising at least a phospholipid such as phosphoryl choline that is useful for coating an implantable device such as a drug eluting stent.

2. Description of the Background

Implanted stents have been used to carry medicinal agents, such as thrombolytic agents. U.S. Pat. No. 5,163,952 to Froix discloses a thermal-memoried expanding plastic stent device formulated to carry a medicinal agent in the material of the stent itself. Pinchuk, in U.S. Pat. No. 5,092,877, discloses a stent of a polymeric material which may have a coating associated with the delivery of drugs. Other patents which are directed to devices of the class utilizing bio-degradable or bio-absorbable polymers include Tang et al., U.S. Pat. No. 4,916,193, and MacGregor, U.S. Pat. No. 4,994,071.

A patent to Sahatjian, U.S. Pat. No. 5,304,121, discloses a coating applied to a stent consisting of a hydrogel polymer and a preselected drug such as cell growth inhibitors or heparin. A further method of making a coated intravascular stent carrying a therapeutic material is described in Berg et al., U.S. Pat. No. 5,464,650, issued on Nov. 7, 1995 and corresponding to European Patent Application No. 0 623 354 A1 published Nov. 9, 1994. In that disclosure, a polymer coating material is dissolved in a solvent and the therapeutic material dispersed in the solvent; the solvent evaporated after application.

An article by Michael N. Helmus entitled "Medical Device Design—A Systems Approach: Central Venous Catheters", 22nd International Society for the Advancement of Material and Process Engineering Technical Conference (1990) relates to polymer/drug/membrane systems for releasing heparin. Those polymer/drug/membrane systems require two distinct types of layers to function.

It has been recognized that contacting blood with the surface of a foreign body in vivo has a tendency to induce thrombogenic responses, and that, as the surface area of a foreign device in contact with host blood increases, the tendency for coagulation and clot forming at these surfaces also increases. This has led to the use of immobilized systemic anti-coagulant or thrombolytic agents such as heparin on blood-contacting surfaces such as blood oxygenator, hemodialysis membrane devices to reduce this phenomenon. Such an approach is described by Winters, et al., in U.S. Pat. Nos. 5,182,317; 5,262,451 and 5,338,770 in which the amine functional groups of the active material are covalently bonded using polyethylene oxide (PEO) on a siloxane surface.

Another approach is described in U.S. Pat. No. 4,613,665 to Larm in which heparin is chemically covalently bound to plastic surface materials containing primary amino groups to impart a non-thrombogenic surface to the material. Other approaches for bonding heparin are described in Barbucci, et al., "Coating of commercially available materials with a new heparinizable material", Journal of Biomedical Materials Research, Vol. 25, pp. 1259-1274 (1991); Hubbell, J. A., "Pharmacologic Modification of Materials", Cardiovascular Pathology, Vol. 2, No. 3 (Suppl.), 121S-127S (1993); Gravlee, G. P., "Heparin-Coated Cardiopulmonary Bypass Circuits", Journal of Cardiothoracic and Vascular Anesthesia, Vol. 8, No. 2, pp. 213-222 (1994). Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent based therapy, the stent can be coated with a biocompatible polymeric coating. The biocompatible polymeric coating can function either as a permeable layer or a carrier to allow a controlled delivery of the agent. A continuing challenge in the art of implantable stents is to provide a coating that possesses good biobeneficial properties, which refer to good biocompatibilities in both the acute and chronic timeframes.

Generally, a polymer forming a coating composition for an implantable device has to be at least biologically benign. Additionally, the polymer could have a therapeutic effect either additively or synergistically with the bioactive agent. The polymer is preferably biocompatible. To provide for a coating that is biologically benign, various compositions have been used with limited success. For example, coating compositions containing poly(ethylene glycol) have been described (see, for example, U.S. Pat. No. 6,099,562). One of the needs in the art is to provide for a coating that has favorable long term biological properties.

Phosphoryl choline (PC) has a zwitterionic functionality that mimics the outer blood-contacting surface of the lipid bilayer structure in blood corpuscles. PC possesses numerous biobeneficial properties such as hemocompatibility, non-thrombogenicity, arterial tissue acceptance and long-term in vivo stability. PC has been used to increase biocompatibility of polymers, especially that of acrylic copolymers.

The polymer and methods of making the polymer disclosed herein address the above described problems.

SUMMARY OF THE INVENTION

Provided herein is a biocompatible polymer comprising choline or phospholipid moieties and a biodegradable or nondegradable polymeric backbone. The phospholipid moieties can be any synthetic and/or natural phospholipids. In one embodiment, the phospholipids include phosphoryl choline, phosphoryl serine, phosphoryl inositol, di-phosphoryl glycerol, zwitterionic phosphoryl ethanolamine, and combinations thereof.

In another embodiment, the nondegradable polymer can be a polymer that comprises any of the following monomers, e.g., methylmethacrylate (MMA), ethylmethacrylate (EMA), butylmethacrylate (BMA), 2-ethylhexylmethacrylate, laurylmethacrylate (LMA), hydroxyl ethyl methacrylate (HEMA), PEG acrylate (PEGA), PEG methacrylate, 2-methacryloyloxyethylphosphorylcholine (MPC) and n-vinyl pyrrolidone (VP), methacrylic acid (MA), acrylic acid (AA), hydroxypropyl methacrylate (HPMA), hydroxypropyl methacrylamide, 3-trimethylsilylpropyl methacrylate (TMSPMA), and combinations thereof. The non-degradable polymer can be, for example, any of ethylene vinyl alcohol copolymer (EVOH), polyurethanes, silicones, polyesters, polyolefins, polyisobutylene and ethylene-alphaolefin copolymers, acrylic polymers and copolymers, vinyl halide polymers and copolymers, polyvinyl chloride, polyvinyl ethers, polyvinyl methyl ether, polyvinylidene halides, polyvinylidene fluoride, polyvinylidene chloride, polyfluoroalkenes, polyperfluoroalkenes, polyacrylonitrile, polyvinyl ketones, polyvinyl aromatics, polystyrene, polyvinyl esters, polyvinyl acetate, copolymers of vinyl monomers with each other and olefins, ethylene-methyl methacrylate copolymers, acrylonitrile-styrene copolymers, ABS resins, and ethylene-vinyl acetate copolymers, polyamides such as Nylon 66 and polycaprolactam, alkyd resins, polyoxymethylenes; polyimides; polyethers, epoxy resins, rayon, rayon-triacetate, and combinations thereof. In another embodiment environmentally sensitive polymers such as temperature sensitive N-isopropyl acrylamide (NIPAAm), pH sensitive polymer dimethyl aminoethyl methacrylate (DMAEM) can be copolymerized with the above PC moieties.

In a further embodiment, the biocompatible polymer can be any biodegradable polymer that comprises any of the following monomers, e.g., glycolide, lactide, butyrolactone, caprolactone, hydroxyalkanoate, 3-hydroxybutyrate, 4-hydroxybutyrate, 3-hydroxyvalerate, 3-hydroxyhexanoate, and combinations thereof. The biodegradable polymers can be, for example, any of polyesters, polyhydroxyalkanoates (PHAs), poly(α-hydroxyacids), poly(β-hydroxyacid) such as poly(3-hydroxybutyrate) (PHB); poly(3-hydroxybutyrate-co-valerate) (PHBV), poly(3-hydroxyproprionate) (PHP), poly(3-hydroxyhexanoate) (PHH), or poly(4-hydroxyacids), poly(4-hydroxybutyrate), poly(4-hydroxyvalerate), poly(4-hydroxyhexanoate), poly(hydroxyvalerate, poly(ester amides) that may optionally contain alkyl; amino acid; PEG and/or alcohol groups, polycaprolactone, polylactide, polyglycolide, poly(lactide-co-glycolide), polydioxanone (PDS), polyorthoester, polyanhydride, poly(glycolic acid-co-trimethylene carbonate), polyphosphoester polyphosphoester urethane, poly(amino acids), polycyanoacrylates, poly(trimethylene carbonate), poly(iminocarbonate), poly(tyrosine carbonates), polycarbonates, poly(tyrosine arylates), polyurethanes, copoly(ether-esters), polyalkylene oxalates, polyphosphazenes, PHA-PEG, and combinations thereof.

In still further embodiment of the present invention, the biocompatible polymer may further comprise a biobeneficial moiety such as a non-fouling moiety, an anti-thrombogenic moiety, or a combination thereof. Representative non-fouling moieties are PEG, polyalkene oxides, hydroxyethylmethacrylate (HEMA), poly(n-propylmethacrylamide), sulfonated polystyrene, hyaluronic acid, poly(vinyl alcohol), poly(N-vinyl-2-pyrrolidone), sulfonated dextran, and combinations thereof. Representative anti-thrombogenic moieties are heparin, salicylate (aspirin), hirudin, flavonoids, NO donor, thrombomodulin, Atrial natriuretic peptide (ANP), and combinations thereof. Various forms of heparin can be used. For example, heparin can be attached to the polymer via a PEG spacer.

The biocompatible polymer described herein can be used alone or in combination with one or more polymers and/or biobeneficial materials, and optionally a bioactive agent. Representative biobeneficial materials include non-fouling materials such as PEG and polyalkene oxides and anti-thrombotic materials such as heparin. Representative bioactive agents include, but are not limited to, proteins, peptides, anti-inflammatory agents, antivirals, anticancer drugs, anticoagulant agents, free radical scavengers, steroidal anti-inflammatory agents, antibiotics, nitric oxide donors, super oxide dismutases, super oxide dismutases mimics, cytostatic agents, prodrugs, co-drugs, and a combination thereof, for example, ABT-578, dexamethasone, clobetasol, paclitaxel, estradiol, 4-amino-2,2,6,6-tetramethylpiperidine-1-oxyl (4-amino-TEMPO), 4-hydroxy-2,2,6,6-tetramethylpiperidine-1-oxyl(TEMPOL), tacrolimus, sirolimus, sirolimus derivatives, 40-O-(2-hydroxyl)ethyl-rapamycin (everolimus), 40-O-(3-hydroxyl)propyl-rapamycin, 40-O-[2-(2-hydroxyl)ethoxy]ethyl-rapamycin, and 40-O-tetrazole-rapamycin, prodrugs, co-drugs, and a combination thereof.

The polymeric compositions described herein can be used to form a coating on an implantable device such as a drug-eluting device (DES). The implantable device can be used for the treatment of a disorder in a human being by implanting in the human being an implantable device as described herein. Such a disorder includes, e.g., atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

DETAILED DESCRIPTION

Coating Composition Comprising at Least a Phospholipid

Provided herein is a biocompatible polymer having a biodegradable or nondegradable polymeric backbone that comprises at least one phospholipid or choline moiety and a degradable or nondegradable polymer. The polymeric backbone can be degradable or nondegradable formed of any biocompatible polymer. Optionally, the polymeric backbone is capable of degrading into components that are pharmacologically active and therapeutic to the process of restenosis or sub-acute thrombosis such as POLYASPIRIN™. POLYASPIRIN™ is a polymer of the following formula:

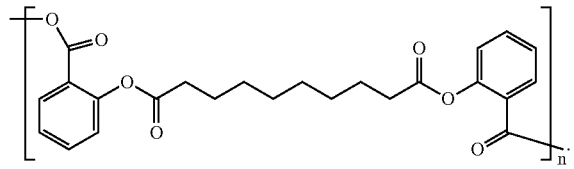

The phospholipid includes, for example, phosphoryl choline, phosphoryl serine, phosphoryl inositol, di-phosphoryl glycerol, zwitterionic phosphoryl ethanolamine, etc, and combinations thereof. The biocompatible polymer can be used to form a coating on an implantable device such as a drug-eluting stent. The coating may optionally include one or more bioactive agents and/or a non-fouling polymer, an anti-thrombogenic polymer, or a combination thereof.

Copolymers Comprising Phospholipid Moieties

In accordance with one aspect of the present invention, it is disclosed herein a copolymer comprising a biocompatible polymer moiety and a phospholipid. The biocompatible polymer can be a biodegradable polymer or a non-degradable polymer. The phospholipids can be any synthetic or natural phospholipids.

Biocompatible Polymers

In one embodiment, the biocompatible polymer useful for making the copolymer comprising a phospholipid moiety is a biodegradable polymer, which can be any biodegradable polymer known in the art. Representative biodegradable polymers include, but are not limited to, polyesters, poly-hydroxyalkanoates (PHAs), poly(ester amides) that may optionally contain alkyl; amino acid; PEG and/or alcohol groups, polycaprolactone, poly(L-lactide), poly(D,L-lactide), poly(D,L-lactide-co-PEG) block copolymers, poly(D, L-lactide-co-trimethylene carbonate), polyglycolide, poly (lactide-co-glycolide), polydioxanone (PDS), polyorthoester, polyanhydride, poly(glycolic acid-co-trimethylene carbonate), polyphosphoester, polyphosphoester urethane, poly(amino acids), polycyanoacrylates, poly(trimethylene carbonate), poly(iminocarbonate), polycarbonates, polyurethanes, copoly(ether-esters) (e.g. PEO/PLA), polyalkylene oxalates, polyphosphazenes, PHA-PEG, and combinations thereof. The PHA may include poly($\alpha$-hydroxy-acids), poly($\beta$-hydroxyacid) such as poly(3-hydroxybutyrate) (PHB); poly(3-hydroxybutyrate-co-valerate) (PHBV); poly(3-hydroxyproprionate) (PHP); poly (3-hydroxyhexanoate) (PHH), or poly(4-hydroxyacid) such as poly(4-hydroxybutyrate); poly(4-hydroxyvalerate); poly (4-hydroxyhexanoate), poly(hydroxyvalerate), poly(tyrosine carbonates), poly(tyrosine arylates).

In another embodiment, the biocompatible polymer useful as moiety of the copolymer comprising phospholipid moieties is a non-degradable polymer. Representative biocompatible, non-degradable polymers include, but are not limited to, ethylene vinyl alcohol copolymer (commonly known by the generic name EVOH or by the trade name EVAL), polyurethanes, silicones, polyesters, polyolefins, polyisobutylene and ethylene-alphaolefin copolymers, styrene-isobutyl-styrene triblock copolymers, acrylic polymers and copolymers, vinyl halide polymers and copolymers such as polyvinyl chloride, poly(vinyldifluoride-co-hexafluoropropane), poly(chlorotrifluoroethylene-co-hexafluoropropane), polyvinyl ethers such as polyvinyl methyl ether, polyvinylidene halides such as polyvinylidene fluoride and polyvinylidene chloride, polyfluoroalkenes, polyperfluoroalkenes, polyacrylonitrile, polyvinyl ketones, polyvinyl aromatics such as polystyrene, polyvinyl esters such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides such as Nylon 66 and polycaprolactam, alkyd resins, polyoxymethylenes; polyimides; polyethers, epoxy resins, rayon, rayon-triacetate, polyurethanes, silk, silk-elastin, polyphosphazenes and combinations thereof.

In a further embodiment, the copolymer described herein comprises one or more of the following hydrophobic monomers: methylmethacrylate (MMA), ethylmethacrylate (EMA), butylmethacrylate (BMA), 2-ethylhexylmethacrylate, laurylmethacrylate (LMA), or combinations thereof. By varying the copolymer's content of the hydrophobic monomers, mechanical properties such as elongation at break and toughness can be modulated. For example, a monomer having a relatively long side chain would enhance the flexibility of a coating comprising the copolymer. In contrast, a monomer having a relatively short side chain would enhance the rigidity and toughness of a coating comprising the copolymer.

In a further embodiment, the copolymer described herein comprises one or more of the following hydrophilic monomers: non-fouling monomers such as hydroxyl ethyl methacrylate (HEMA), PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, 3-trimethylsilylpropyl methacrylate (TMSPMA), and combinations thereof. The carboxylic acid bearing monomers or hydroxyl bearing monomers can be used to crosslink the copolymer once it is applied to the substrate to coat. This will hinder a very hydrophilic coating from dissolving away.

Phospholipids

In one embodiment, the phospholipids useful for making a copolymer with a biocompatible polymer can be neutral, positively charged or negatively charged synthetic phospholipids. Representative useful synthetic phospholipids include, but are not limited to, semi-synthetic phosphoryl choline such as cardiolipin or sphingosine.

In another embodiment, the phospholipids useful for making a copolymer with a biocompatible polymer can be neutral, positively charged or negatively charged natural phospholipids. Representative useful natural phospholipids include, but are not limited to, phosphoryl choline, phosphoryl serine, phosphoryl inositol, di-phosphoryl glycerol, or zwitterionic phosphoryl ethanolamine, and combinations thereof.

In a further embodiment, the phospholipid useful for making a copolymer with a biocompatible polymer can be phosphoryl choline. Phosphoryl choline (PC) is a zwitterionic functionality that mimics the outer surface of a lipid bilayer. It has good hemocompatibility, non-thrombogenicity, arterial tissue acceptance and long-term in-vivo stability. It has been used to increase the biocompatibility of polymers, especially of acrylic copolymers.

Methods of Making Copolymers Comprising Phospholipids

The copolymer described herein can be synthesized by introducing the phospholipids moiety into a polymer. The phospholipid moieties can be introduced into the polymer via a reactive functionality, which can be, for example, hydroxyl groups, amino groups, halo groups, carboxyl groups, thiol groups, aldehyde, N-hydroxysuccinimide (NHS). Alternatively, a phospholipid moiety can be introduced into a monomer such as an oxirane. Polymerization of the monomer can generate a polymer bearing phospholipids moieties.

In one embodiment, a monomer bearing a protected hydroxyl functionality can be copolymerized with an oxirane, for example lactide or caprolactone, etc., or incorporated into a polymer such as a polyester amide backbone. The hydroxyl functionality then can be deprotected and subsequently converted to a phospholipid functionality, for example, a PC functionality. The protective group can be the any of the ones that are easily removable and thus would not interfere with the polymerization.

The synthesis of polymerizable monomers bearing protected hydroxyl groups is illustrated in Schemes 1 and 2. Scheme 1 illustrates an exemplary method of introducing a PC functionality into a polymerizable monomer via the synthesis of a benzyl ester protected hydroxyl functional caprolactone. Cyclohexane-1,4-diol can be oxidized by an oxidizing agent, for example a mixture of NaBrO$_3$ and (NH$_4$)$_2$Ce(NO$_3$)$_6$, to form 4-hydroxyl-cyclohexanone. The hydroxyl group can be protected using a protective agent such as benzyl bromide to protect the hydroxyl group, forming, for example, 4-benzoxycyclohexanone, which can react with a peroxyacid such as 4-chlorobenzoic peroxyacid to form a caprolactone bearing a benzyl group protected hydroxyl functionality. Other useful protective groups include, for example, tert-butyldimethylsilyl (TBDMS), N-tert-butoxycarbonate (t-BOC), and N(9-fluorenyl-methoxycarbonyl) (FMOC).

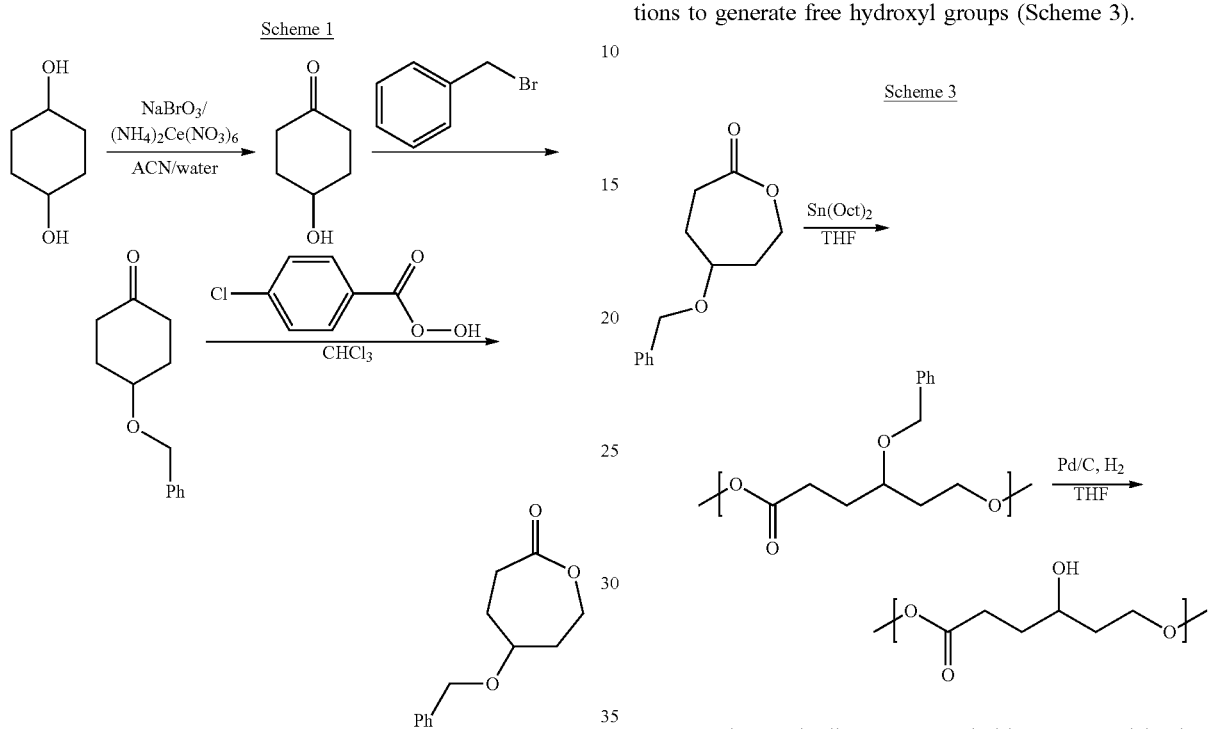

Scheme 2 illustrates another embodiment of the method described herein. A protected hydroxyl aldehyde such as benzoxyacetaldehyde can undergo cyclization with a halo acyl compound such as acetyl bromide in the presence of a catalyst such as $AlCl_3/AgSbF_6$ (in the presence of a base such as (DIEA) diisopropylethylamine to form a butyrolactone such as β-benzoxymethylbutyrolactone.

Monomers bearing a protected reactive functionality can undergo polymerization alone or copolymerization with other comonomers to form polymers or copolymers bearing protected functionalities. For example, the substituted ε-caprolactone and β-butyrolactone can be copolymerized with glycolide, lactide, or an oxirane such as butyrolactone, valerolactone, or caprolactone to form a polymer or copolymer with different compositions. In one embodiment, a benzyl protected caprolactone can polymerize in the presence of a catalyst such as dioctylstannane ($Sn(Oct)_2$) to yield a polycaprolactone with benzyl protected hydroxyl groups. The benzyl groups can be cleaved off under acidic conditions to generate free hydroxyl groups (Scheme 3).

In another embodiment, any suitable compound having three hydroxyl groups can be protected with a protective group such as a benzyl group. The remaining two free hydroxyl groups can react with an amino acid and be subsequently incorporated into a poly(ester amide) backbone (Scheme 4). Alternatively, a molecule with two amine groups and one hydroxyl group can be used to incorporate a protected hydroxyl group into the poly(ester amide) backbone (Scheme 4). The protective group can then be removed as described above to generate free hydroxyl groups.

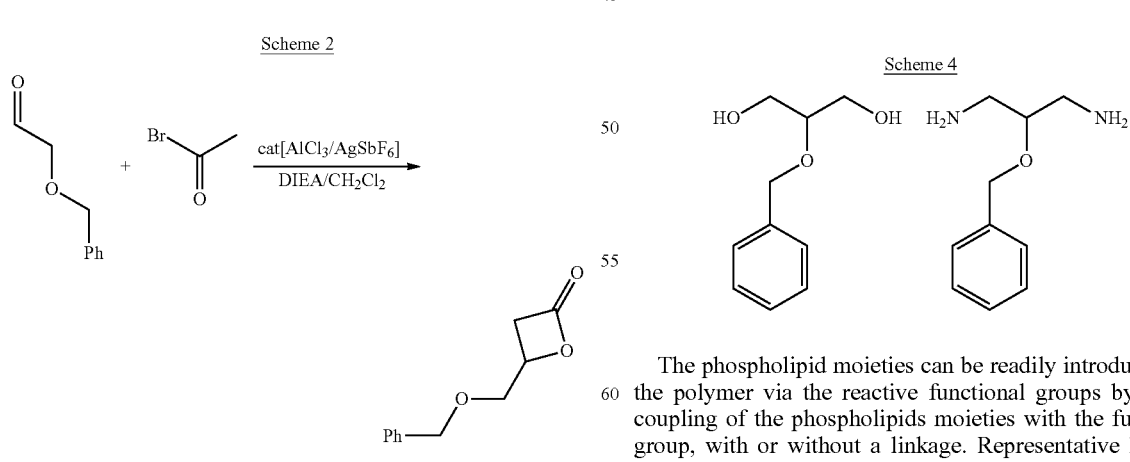

The phospholipid moieties can be readily introduced into the polymer via the reactive functional groups by simple coupling of the phospholipids moieties with the functional group, with or without a linkage. Representative linkages can be hydroxyl, amino, carboxyl, thiol, or other groups with or without a spacer such as poly(ethylene glycol), etc. Alternatively the phospholipid moieties can be synthesized in situ via standard organic reactions (see embodiment below).

In one embodiment, the PC functionalities can be introduced into a polymer bearing hydroxyl groups according to Scheme 5. The polymer, which has a repeating unit designated as

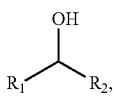

is allowed to react with an agent such as ethylene chlorophosphate to form an ethylene phosphate derivative of the polymer. The ethylene phosphate functionality can react with an amine such as trimethylamine at a temperature such as about 60° C. to generate the PC functionality (Scheme 5).

Scheme 5

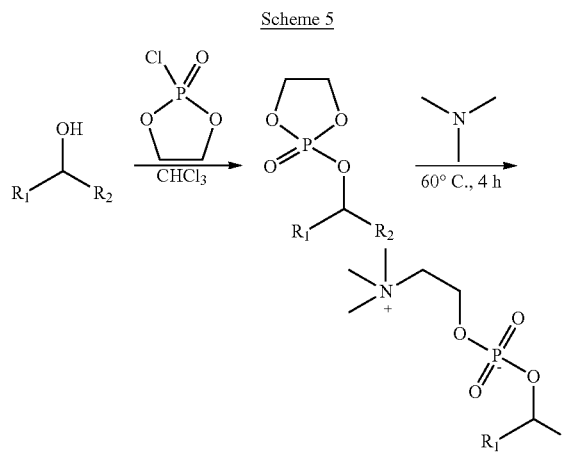

Monomers bearing a phospholipid moiety can polymerize alone or with other comonomers, with or without phospholipid moieties, by means known in the art e.g., catalytic polymerization, chemical reaction, or free radical polymerization, to form respective polymers bearing phospholipid moieties. For example, MPC, an olefinic monomer bearing a phosphoryl choline functionality, can readily polymerize, alone or with one or more other comonomers, by free radical polymerization to form a polymer bearing phosphoryl choline moieties.

Biobeneficial Polymers

In another aspect of the present invention, the composition described herein may include one or more biobeneficial polymers including non-fouling polymers and anti-thrombogenic agents. Various non-fouling polymers are known in the art. Exemplary non-fouling polymers include PEG, polyalkene oxides, hydroxyethylmethacrylate (HEMA), poly(n-propylmethacrylamide), sulfonated polystyrene, hyaluronic acid, poly(vinyl alcohol), poly(N-vinyl-2-pyrrolidone), sulfonated dextran, and combinations thereof. Representative anti-thrombogenic moieties are heparin, salicylate (aspirin), hirudin, flavonoids, NO donor, thrombomodulin, Atrial natriuretic peptide (ANP), and combinations thereof. The non-fouling polymer can be used together with the polymers comprising phospholipid moieties as a blend or can be incorporated into the backbone of the polymers comprising phospholipid moieties.

In one embodiment, the non-fouling polymer is PEG. PEG is commonly used as a non-fouling surface material in biomedical applications. PEG is water-soluble and must be covalently attached to a hydrophobic backbone or to a crosslinked polymer to yield long-term benefits. PEG can readily be incorporated into the backbone of any of the copolymers by, for example, coupling the hydroxyl, amino, or carboxylic acid terminated PEG with the pendant functional groups such as carboxylic acids or hydroxyls in the backbone of the copolymer by a linking agent such as carbodiimide chemistry (1,3-dicyclohexylcarbodiimide (DCC), 1-(3-dimethylaminopropyl)-3-ethylcarbodiimide (EDC) and other Mitsunobu reagents). The PEG useful for coupling with the hydrophobic backbone of the phospholipid containing polymer has a molecular weight in the range between about 300 daltons and about 40,000 daltons.

In another embodiment, the biobeneficial polymer is heparin. Heparin is commonly used as an anti-thrombogenic agent. Heparin can be coupled via a spacer such as PEG to a polymer backbone containing functional groups such as carboxylic acids. In one embodiment, the coupling can be carried out using an aldehyde terminated heparin, which can be coupled to a PEG diamine where one amine is protected with a protective group such as t-BOC. Upon removal of the protective group, the second amine can be coupled to a carboxylic group on the polymer backbone using a linking agent such as 1,3-dicyclohexylcarbodiimide (DCC), 1-(3-dimethylaminopropyl)-3-ethylcarbodiimide (EDC) and other Mitsunobu reagents. In another embodiment, 2-(dimethylamino)ethyl methacrylate (DMAEMA) can also be incorporated into the backbone and used to ionically coordinate or conjugate with heparin.

In a further embodiment, PEG and heparin are both incorporated into the polymer comprising the phospholipid moieties. In one embodiment, a polymer having a methacrylate backbone can be made to contain 2-methacryloyloxyethylphosphorylcholine and 2-aminoethyl methacrylamide. Aldehyde terminated heparin, which is commercially available, can be coupled to the terminal amino group via reductive amination using sodium cyanoborohydride (Scheme 6).

Scheme 6

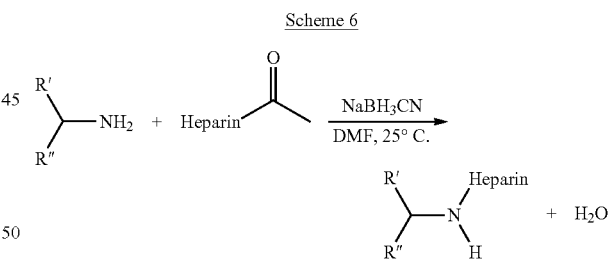

This heparin coupling can be done either before, or after, a topcoat, comprising a polymer having a methacrylate backbone that contains 2-methacryloyloxyethylphosphorylcholine and 2-aminoethyl methacrylamide, is placed onto an implantable device such as a DES. A topcoat comprising both the PEG and heparin and a phospholipid (for example, PC) containing polymer is non-fouling and anti-thrombogenic. If desirable, other non-fouling and/or anti-thrombogenic moieties can be incorporated into the topcoat.

Bioactive Agents

The bioactive agent can be any agent which is biologically active, for example, a therapeutic, prophylactic, or diagnostic agent. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 or more grams per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

In the case of controlled release of agents, a wide range of different bioactive agents can be incorporated into a controlled release device. These include hydrophobic, hydrophilic, and high molecular weight macromolecules such as proteins. The bioactive compound can be incorporated into polymeric coating in a percent loading of between 0.01% and 70% by weight, more preferably between 5% and 50% by weight.

In one embodiment, the bioactive agent can be for inhibiting the activity of vascular smooth muscle cells. More specifically, the bioactive agent can be aimed at inhibiting abnormal or inappropriate migration and/or proliferation of smooth muscle cells for the inhibition of restenosis. The bioactive agent can also include any substance capable of exerting a therapeutic or prophylactic effect in the practice of the present invention. For example, the bioactive agent can be for enhancing wound healing in a vascular site or improving the structural and elastic properties of the vascular site. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, ABT-578, dexamethasone, clobetasol, paclitaxel, estradiol, 4-amino-2,2,6,6-tetramethylpiperidine-1-oxyl (4-amino-TEMPO), 4-hydroxy-2,2,6,6-tetramethylpiperidine-1-oxyl(TEMPOL), tacrolimus, sirolimus, sirolimus derivatives, 40-O-(2-hydroxy)ethyl-rapamycin (EVEROLIMUS), 40-O-(3-hydroxy)propyl-rapamycin, 40-O-[2-(2-hydroxy)ethoxy]ethyl-rapamycin, and 40-O-tetrazole-rapamycin, prodrugs, co-drugs, and a combination thereof. The foregoing substances are listed by way of example and are not meant to be limiting. Other active agents which are currently available or that may be developed in the future are equally applicable.

Useful bioactive agents also include prodrugs and co-drugs of the agents described herein.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the trauma; the nature of the therapy desired; the time over which the administered ingredient resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Coating Constructs

The copolymers described herein can be used to form coating compositions for coating on an implantable device, for example, a drug-eluting stent (DES). The copolymer comprising at least one phospholipid moiety can be used alone or in combination with another polymer. For use as DES coatings, the composition can include a bioactive agent.

The coatings described herein can have various configurations. In one embodiment, the coating can be formed with the copolymer described herein alone or in combination with other polymers. Useful other polymers include the degradable and non-degradable biocompatible polymers described above. The copolymers described herein can be used to form a topcoat on DES on top of a drug reservoir coating that does not contain the copolymers comprising the PC moieties. For example, a DES can be made to have a coating that has a primer layer comprising a polymer such as poly(n-butyl methacrylate) (PBMA), a drug reservoir layer comprising a biocompatible, biodegradable or non-degradable polymer as described above with no phospholipid moieties such as ethylene vinyl alcohol (EVAL) or polyvinylidene fluoride (PVDF), and finally a topcoat with a copolymer described herein that comprises phospholipid moieties such as PC methacrylate. The topcoat may further comprise a polymer with no phospholipid moieties such as PBMA.

In another embodiment, the coating may comprise a copolymer comprising phospholipids moieties in all the layers of the coating. For example, a DES coating can be formed to have a primer layer that comprises about 1-5 wt % PBMA-PC, a layer of reservoir that comprises PBMA and about 1-20 wt % PBMA-PC, and a topcoat that comprises PBMA and 25-50 wt % PBMA-PC.

In another embodiment, the coating can be made to comprise layers having a copolymer that comprises phospholipid moieties in a concentration gradient in the various layers with a concentration of the copolymer that is higher in the topcoat, decreasing to the lowest concentration in the primer layer. For example, the copolymer can be PBMA-PC.

In a further embodiment, the coating construct can be made to release two or more drugs. In one embodiment, if desirable, the second drug can be blended into the matrix with the first drug such as ABT-578 or everolimus such that the second drug can be released in the same time frame with the first drug. In another embodiment, if the second drug is hydrophilic and it is desirable to have a quick release of the second drug, it can be blended with the topcoat comprising phospholipid moieties such as PC moieties. Such hydrophilic drugs include peptides such as cyclic RGD, aspirin, nitric oxide donors, and stable nitroxides, etc. The second drug can also be swell-loaded into the applied topcoat. Additional drugs can be loaded onto the coat in the drug reservoir or topcoat.

Methods of Using the Coating Composition

The coating composition can be coated onto any implantable device by any established coating process, e.g., a spray process. Generally, the coating process involves dissolving or suspending the composition in a solvent to form a solution or a suspension of the coating composition, and then applying the solution or suspension to an implantable device such as a DES.

As used herein, an implantable device may be any suitable medical substrate that can be implanted in a human or veterinary patient. A preferred implantable device is DES. Examples of stents include self-expandable stents, balloon-expandable stents, and stent-grafts. Other exemplary implantable devices include grafts (e.g., aortic grafts), artificial heart valves, cerebrospinal fluid shunts, pacemaker electrodes, and endocardial leads (e.g., FINELINE® and ENDOTAK,® available from Guidant Corporation, Santa Clara, Calif.). The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR® 108, cobalt chrome alloy L-605, "MP35N," "MP20N," ELASTINITE® (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

EXAMPLES

The embodiments of the present invention will be illustrated by the following set forth examples. All parameters and data are not to be construed to unduly limit the scope of the embodiments of the invention.

Example 1

P(MPC-PEGA-BMA) Copolymer

The components, 2-methacryloyloxyethyl phosphorylcholine (MPC) butylmethacrylate (BMA), poly(ethylene glycol) acrylate (PEGA) (Mn=350 Da) and AIBN ($\alpha,\alpha'$-azobutyronitrile) were dissolved in ethanol at a molar ratio of (15:10:74:1). The reactants were maintained at 62° C. for 24 h. The polymer was purified, by a double precipitation in methanol, to yield a white powder.

A first composition was prepared by mixing the following components:
(a) about 2 mass % poly(butyl methacrylate) (PBMA);
(b) dissolved in a mixture of acetone and cyclohexanone (30% and 70% respectively).

The first composition was applied onto the surface of a bare 12 mm VISION® stent (available from Guidant Corporation) by spraying and dried to form a stent coating. A spray coater was used, having a 0.014 fan nozzle maintained at ambient temperature with a feed pressure of about 0.2 atm (about 3 psi) and an atomization pressure of about 1.3 atm (about 20 psi). About 20 µg of the wet coating was applied per pass. Between the passes, the coating was dried at about 50° C. for about 10 seconds. Following the last pass, the coating was baked at about 50° C. for about 1 hour, yielding a dry primer layer. The dry primer layer contained about 80 µg of PBMA.

A second composition was prepared by mixing the following components:
(a) about 2 mass % SOLEF®; and
(b) about 0.7 mass % everolimus; and
(c) the balance, a mixture of acetone and cyclohexanone (30% and 70% respectively.

The second composition was applied onto the dry primer layer using the same coating technique and conditions as for making the primer layer, yielding a dry reservoir layer. The dry reservoir layer contained about 430 µg of Solef and 150 µg of everolimus. The total weight of the coating was about 580 µg.

A third composition was prepared by mixing the following components:
(a) about 2 mass % p(MPC-PEGA-BMA); and
(b) the balance, a mixture of acetone and dimethylformamide (50% and 50% respectively.

The third composition was applied onto the dry reservoir layer using the same coating technique and conditions as for making the primer layer, yielding a dry topcoat layer. The dry topcoat layer contained about 100 µg of p(MPC-PEGA-BMA).

16 stents were coated as described above. 8 stents were sterilized using electron beam sterilization at a dose of 25 KGy as known to those having ordinary skill in the art, and the other 8 stents were not sterilized.

Example 2

Hydroxyl Functional Caprolactone

A 100 g 1,4-hexanediol was dissolved in 1.4 L of a mixture of acetonitrile and water (7:3 by volume). A mixture of 45.4 g of sodium bromate and 16.5 g of ammonium cerium (IV) nitrate was slowly added. The reaction was maintained under reflux conditions for 90 min. Once acetonitrile was removed by rotary evaporation, the solution was diluted with 800 mL of water and continuously extracted with chloroform for 72 h. The organic solution was dried over magnesium sulfate. Finally chloroform was evaporated from the organic solution to yield 99.5 g of a colorless oil (4-hydroxycyclohexanone).

130 g of benzyl chloride were slowly added to a solution of 60 g of 4-hydroxycyclohexanone in 400 mL of triethylamine. The solution was left to react at 25° C. for 2 h. After removal of the solvent, the product was purified by column chromatography to yield 100 g of a white powder 4-benzylestercyclohexanone.

To a solution of 20 g 3-chloroperoxybenzoic acid in 200 mL of chloroform was added a solution of 15 g of 4-benzylestercylohexanone in 100 mL of chloroform. The reaction proceeded at 25° C. for 14 h. The solution was passed through Celite™, extracted with brine and water successively. The solution was dried over magnesium sulfate and the solvent evaporated. Finally, the product was re-crystallized from a solution of ethyl acetate:hexane (1:4) to yield 7 g of white powder, benzylester protected 4-hydroxylcaprolactone (p-CLOH).

50 mg of 1,6-hexandiol, 20 g of D,L lactide (DLL) monomer and 4 g of p-CLOH were dried by azeotropic distillation of toluene. The monomers were heated to 140° C. to add stannous octoate (0.5 mol %) under a blanket of argon. The reaction was left to proceed at 160° C. for 14 h. The resulting polymer poly(DLL-pCLOH) was dissolved in acetone, precipitated in methanol and dried under reduced pressure.

The benzyl protecting group was removed by dissolving 10 g of poly(DLL-pCLOH) in 100 ml of anhydrous ethyl acetate and adding 0.8 g of tin(IV) chloride under a blanket of argon. The reaction proceeded at 25° C. for 90 min. The resulting polymer poly(DLL-CLOH) was precipitated in methanol and dried under reduced pressure.

To 4 g of poly(DLL-CLOH) dissolved in 20 mL of predried dichloromethane, was added 1.5 eq. of dry pyridine and was cooled to −5° C. A solution of ethylene chlorophosphate (0.5 mg) in 5 mL of dry chloroform was added dropwise and reacted for 2 h at −5° C. The resultant solution was allowed to reach 25° C. and react for 4 more h. The resulting solution was diluted with 50 mL dichloromethane, and then extracted with distilled water and a 1 M solution of NaHCO$_3$. The organic phase was dried with sodium sulfate and filtered to yield poly(DLL-CLP).

Three (3) g of poly(DLL-CLP) were dissolved in 30 mL of dry acetonitrile and cooled to −10° C. Approximately 300 µL of trimethylamine was condensed into the pressure vessel, which was then slowly heated to 60° C. The solution was stirred for 45 h at this temperature. The resulting polymer, a copolymer of d,l-lactide and caprolactone bearing phosphorylcholine pendant groups (poly(DLL-CLPC)), was precipitated in methanol and dried under reduced pressure.

A first composition was prepared by mixing the following components:
    (a) about 2 mass % poly(D,L lactide); was
    (b) dissolved in a mixture of acetone and cyclohexanone (75% and 25% respectively).

The first composition was applied onto the surface of a bare 12 mm VISION® stent (available from Guidant Corporation) by spraying and dried to form a stent coating. A spray coater was used, having a 0.014 fan nozzle maintained at ambient temperature with a feed pressure of about 0.2 atm (about 3 psi) and an atomization pressure of about 1.3 atm (about 20 psi). About 20 µg of the wet coating was applied per pass. Between the passes, the coating was dried at about 50° C. for about 10 seconds. Following the last pass, the coating was baked at about 50° C. for about 1 hour, yielding a dry reservoir layer. The dry primer layer contained about 75 µg of poly(D,L lactide).

A second composition was prepared by mixing the following components:
    (a) about 2 mass % poly(D.L lactide) ; and
    (b) about 0.7 mass % everolimus; and
    (c) the balance, a mixture of acetone and cyclohexanone (75% and 25%, respectively).

The second composition was applied onto the dry primer layer using the same coating technique and conditions as for making the primer layer, yielding a dry reservoir layer. The dry reservoir layer contained about 200 µg of poly(D,L-lactide) and 100 µg of everolimus.

A third composition was prepared by mixing the following components:
    (a) about 2 mass % p(DLL-CLPC); and
    (b) the balance, a mixture of acetone and cyclohexanone (75% and 25%, respectively).

The third composition was applied onto the dry reservoir layer using the same coating technique and conditions as for making the primer layer, yielding a dry topcoat layer. The dry topcoat layer contained about 80 µg of p(DLL-CLPC).

16 stents were coated as described above. 8 stents were sterilized using electron beam sterilization method at a dose of 25 KGy as known to those having ordinary skill in the art, and the other 8 stents were not sterilized.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable device comprising a coating comprising a biocompatible polymer having a biodegradable or nondegradable polymeric backbone, comprising:
    a biodegradable or nondegradable polymer; and
    a moiety, the moiety being phosphoryl inositol, cardiolipin, or a combination thereof.

2. The implantable device of claim 1 wherein the polymeric backbone of the biocompatible polymer is nondegradable, and the nondegradable polymer is formed from one or more monomers, at least one monomer selected from the group consisting of methylmethacrylate (MMA), ethylmethacrylate (EMA), butylmethacrylate (BMA), 2-ethylhexylmethacrylate, laurylmethacrylate (LMA), hydroxyl ethyl methacrylate (HEMA), polyethylene glycol (PEG) acrylate, PEG methacrylate, 2-methacryloyloxyethylphosphorylcholine (MPC), n-vinyl pyrrolidone (VP), methacrylic acid (MA), acrylic acid (AA), hydroxypropyl methacrylate (HPMA), hydroxypropylmethacrylamide, 3-trimethylsilyl-propyl methacrylate (TMSPMA), and combinations thereof.

3. The implantable device of claim 1 wherein the polymeric backbone of the biocompatible polymer is biodegradable, and the biodegradable polymer comprises monomers selected from the group consisting of glycolide, lactide, butyrolactone, caprolactone, hydroxyalkanoate, 3-hydroxybutyrate, 4-hydroxybutyrate, 3-hydroxyvalerate, 3-hydroxyhexanoate, and combinations thereof.

4. The implantable device of claim 1 wherein the polymeric backbone of the biocompatible polymer is biodegradable, and the biodegradable polymer is selected from the group consisting of polyesters, polyhydroxyalkanoates (PHAs), poly(α-hydroxyacids), poly(β-hydroxyacid)s, poly(3-hydroxybutyrate) (PHB), poly(3-hydroxybutyrate-co-valerate) (PHBV), poly(3-hydroxyproprionate) (PHP), poly(3-hydroxyhexanoate) (PHH), poly(4-hydroxyacids), poly(4-hydroxybutyrate), poly(4-hydroxyvalerate), poly(4-hydroxyhexanoate), poly(hydroxyvalerate, poly(ester amides), polycaprolactone, polylactide, polyglycolide, poly(lactide-co-glycolide), polydioxanone (PDS), polyorthoesters, polyanhydrides, poly(glycolic acid-co-trimethylene carbonate), polyphosphoesters polyphosphoester urethanes, poly(amino acids), polycyanoacrylates, poly(trimethylene carbonate), poly(iminocarbonate), poly(tyrosine carbonates), polycarbonates, poly(tyrosine arylates), polyurethanes, copoly(ether-esters), polyalkylene oxalates, polyphosphazenes, PHA-PEG, and combinations thereof.

5. The implantable device of claim 1 wherein the polymeric backbone of the biocompatible polymer is nondegradable, and the nondegradable polymer is selected from the group consisting of ethylene vinyl alcohol copolymer (EVOH), polyurethanes, silicones, polyesters, polyolefins, polyisobutylene and ethylene-alphaolefin copolymers, styrene-isobutylene-styrene triblock copolymers, acrylic polymers and copolymers, vinyl halide polymers and copolymers, polyvinyl chloride, polyvinyl ethers, polyvinyl methyl ether, polyvinylidene halides, polyvinylidene chloride, polyfluoroalkenes, polyperfluoroalkenes, polyacrylonitrile, polyvinyl ketones, polyvinyl aromatics, polystyrene, polyvinyl esters, polyvinyl acetate, copolymers of vinyl monomers with each other and olefins, ethylene-methyl methacrylate copolymers, acrylonitrile-styrene copolymers, ABS resins, ethylene-vinyl acetate copolymers, polyamides, alkyd resins, polyoxymethylenes, polyimides, polyethers, epoxy resins, rayon, rayon-triacetate, and combinations thereof.

6. The implantable device of claim 1 further comprising a biobeneficial moiety selected from the group consisting of non-fouling moieties, anti-thrombogenic moieties, and combinations thereof.

7. The implantable device of claim 6 wherein the biobeneficial moiety is a non-fouling moiety or a combination of a non-fouling moiety and one or more additional biobeneficial agents, and the non-fouling moiety is selected from the group consisting of PEG, polyalkene oxides, hydroxyethylmethacrylate (HEMA), poly(n-propylmethacrylamide), sulfonated polystyrene, hyaluronic acid, poly(vinyl alcohol), poly(N-vinyl-2-pyrrolidone), sulfonated dextran, and combinations thereof.

8. The implantable device of claim 7 wherein the non-fouling moiety is heparin or heparin and one or more other non-fouling moieties, and wherein the heparin is attached to the polymer via a PEG spacer.

9. The implantable device of claim 6, wherein the biobeneficial moiety is an anti-thrombogenic moiety, or a combination of an anti-thrombogenic moiety and one or more additional biobeneficial agents, the anti-thrombogenic moiety being selected from the group consisting of heparin, salicylate (aspirin), hirudin, flavonoids, NO donor, thrombomodulin, Atrial natriuretic peptide (ANP), and combinations thereof.

10. The implantable device of claim 1 wherein the polymeric backbone of the biocompatible polymer comprises the polymer of the formula

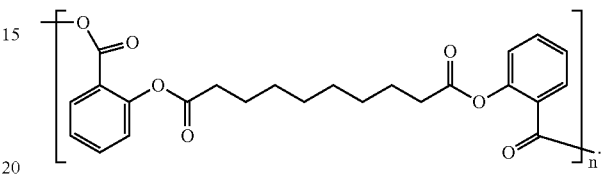

11. The implantable device of claim 1, wherein the coating further comprises a bioactive agent.

12. The implantable device of claim 1, wherein the bioactive agent is selected from the group consisting of ABT-578, dexamethasone, clobetasol, paclitaxel, estradiol, 4-amino-2,2,6,6-tetramethylpiperidine-1-oxyl (4-amino-TEMPO), 4-hydroxy-2,2,6,6-tetramethylpiperidine-1-oxyl (TEMPOL), tacrolimus, sirolimus, 40-O-(2-hydroxy)ethyl-rapamycin (everolimus), 40-O-(3-hydroxy)propyl-rapamycin, 40-O-[2-(2-hydroxy)-ethoxy]ethyl-rapamycin, 40-O-tetrazole-rapamycin, and combinations thereof.

13. The implantable device of claim 1, which is a stent.

14. The implantable device of claim 11, which is a stent.

15. The implantable device of claim 12, which is a stent.

16. A method of treating a human being suffering from a disorder by implanting in the human being the implantable device as defined in claim 11,
wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

17. A method of treating a human being suffering from a disorder by implanting in the human being the implantable device as defined in claim 12,
wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

18. A method of treating a human being suffering from a disorder by implanting in the human being the implantable device as defined in claim 15,
wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

* * * * *